United States Patent [19]

Sasaki et al.

[11] Patent Number: 4,996,362

[45] Date of Patent: Feb. 26, 1991

[54] 5-[(4-N,N-DITOLYLAMINO)BENZYL]-5H-DIBENZO[A,D]-CYCLOHEPTANE DERIVATIVES

[75] Inventors: Masaomi Sasaki, Susono; Tamotsu Aruga, Mishima, both of Japan

[73] Assignee: Ricoh Company, Ltd., Tokyo, Japan

[21] Appl. No.: 520,066

[22] Filed: May 3, 1990

[30] Foreign Application Priority Data

May 31, 1989 [JP] Japan .................. 1-140106

[51] Int. Cl.$^5$ ............................ C07C 211/54
[52] U.S. Cl. ........................ 564/315; 564/433
[58] Field of Search ........................... 564/315

[56] References Cited

U.S. PATENT DOCUMENTS 4,769,302  9/1988  Ueda .......................... 564/315

FOREIGN PATENT DOCUMENTS 0857113  8/1981  U.S.S.R. ...................... 564/315

*Primary Examiner*—Glennon H. Hollrah
*Assistant Examiner*—Susan P. Treanor
*Attorney, Agent, or Firm*—Oblon, Spivak, McClelland, Maier & Neustadt

[57] ABSTRACT

5-[(4-N,N-ditolylamino)benzyl]-5H-dibenzo[a,d]-cycloheptane derivatives having formula (I), which are useful as organic photoconductive materials in electrophotography.

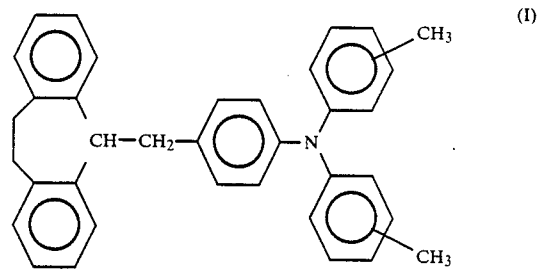

2 Claims, 1 Drawing Sheet

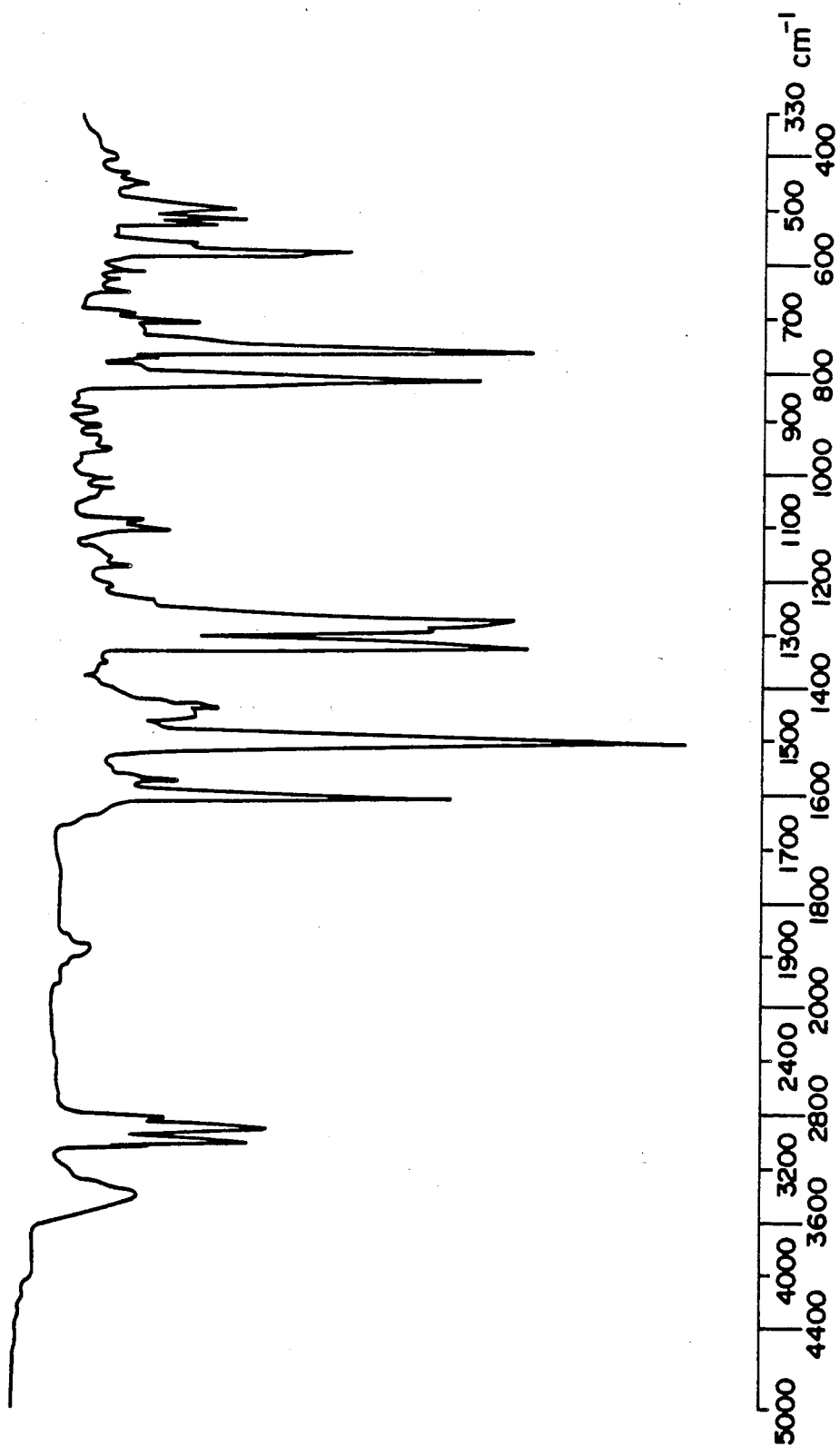
FIGURE

5-[(4-N,N-DITOLYLAMINO)BENZYL]-5H-DIBENZO[A,D]-CYCLOHEPTANE DERIVATIVES

BACKGROUND OF THE INVENTION

1. Field of the Invention

The present invention relates to 5-[(4-N,N-ditolylamino)benzyl]-5H-dibenzo[a,d]-cycloheptane derivatives which are effective as organic photoconductive materials for use in electrophotography.

2. Discussion of Background

Various organic photoconductive materials have been conventionally proposed for use in an electrophotographic process. For example, poly-N-vinylcarbazole and triphenylamine compounds are disclosed in U.S. Pat. No. 3,180,730; and benzidine compounds in U.S. Pat. No. 3,265,496, Japanese Patent Publication 39-11546 and Japanese Laid-Open Patent Application 53-27033.

In the above-mentioned electrophotographic process, the surface of a photoconductor is charged uniformly in the dark to a predetermined polarity, for instance, by corona charging. The uniformly charged photoconductor is exposed to a light image to selectively dissipate the electrical charge of the exposed areas, so that a latent electrostatic image is formed on the photoconductor. The thus formed latent electrostatic image is developed by a developer or toner to a visible image.

Fundamental characteristics required for the photoconductor in such an electrophotographic process are: (1) chargeability to an appropriate potential in the dark, (2) minimum dissipation of electrical charge in the dark, and (3) rapid dissipation of electrical charge when exposed to the light.

However, the above-mentioned conventional organic photoconductive materials do not necessarily satisfy the above characteristics at the same time.

SUMMARY OF THE INVENTION

Accordingly, an object of the present invention is to provide photoconductive materials which can satisfy all the fundamental requirements for use in the electrophotographic process.

The above-mentioned object of the present invention can be achieved by 5-[(4-N,N-ditolylamino)benzyl]-5H-dibenzo[a,d]-cycloheptane derivatives having the following formula (I).

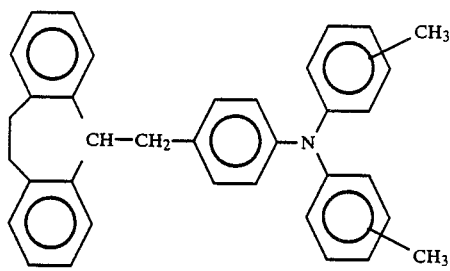

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

Single figure is an infrared absorption spectrum of a 5-[4-N,N-ditolylamino)benzyl]-5H-dibenzo[a,d]-cycloheptane derivative according to the present invention, taken by use of a KBr tablet.

DESCRIPTION OF THE PREFERRED EMBODIMENTS

5-[4-N,N-ditolylamino)benzyl]-5H-dibenzo[a,d]-cycloheptane derivatives of formula (I) according to the present invention, which are novel materials, can be prepared by hydrogenerating cycloheptene derivatives having formula (II):

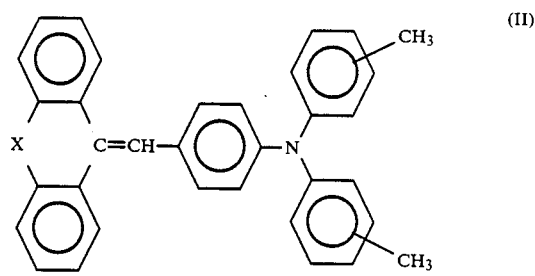

wheretin X represents —$CH_2$—$CH_2$— or —CH=CH—.

The above hydrogeneration reaction is carried out by use of either homogeneous catalysts or heterogeneous catalysts.

Examples of the homogeneous catalysts for use in the present invention are complex compounds of metallic elements belonging to the group VIII in the periodic table of elements, such as rhodium, ruthenium, iridium and cobalt.

Examples of the heterogeneous catalysts for use in the present invention are platinum compounds, Raney nickel catalysts, and catalysts constructed in such a fashion that platinum, palladium, rhodium or ruthenium is supported by activated carbon, alumina or barium sulfate.

In the present invention, the above-mentioned heterogeneous catalysts are preferable from the viewpoint of the convenience of after-treatment.

When the heterogeneous catalyst is employed in the reaction, the reduction is initiated by vigorously stirring the compound to be reduced, with the atmosphere replaced with hydrogen gas of 1 atm., in a closed system. The hydrogen gas is supplied to the reaction system through a pressure reducing valve, as absorbed in the course of the reaction. When the stoichiometric amount of the hydrogen gas is absorbed by the above cycloheptene derivative, the absorption is terminated, and the reduction is completed. The reaction may be carried out at room temperature. In the case where the hydrogen gas is not readily absorbed by the cycloheptene derivative, the system may be heated in the course of the reduction.

Examples of the reaction solvent for use in the hydrogeneration are methanol, ethanol, propanol, tetrahydrofuran, dioxane and ethyl acetate.

The 5-[(4-N,N-ditolylamino)benzyl]-5H-dibenzo[a,d]-cycloheptane derivatives having formula (I) according to the present invention are remarkably effective as photoconductive materials in the electrophotographic photoconductor and can be optically or chemically sensitized with sensitizers such as dyes or Lewis acids. In addition, 5-[(4-N,N-ditolylamino)benzyl]-5H-dibenzo[a,d]-cycloheptane derivatives having formula (I) effectively function as charge transporting materials in a function-separating type electrophotographic photoconductor in which an organic or inorganic pigment is as a charge generating material.

Specific examples of the previously mentioned sensitizers are triarylmethane dyes such as Methyl Violet and Crystal Violet; xanthene dyes such as Rose Bengale, Erythrosin and Rhodamine; thiazine dyes such as Methylene Blue; and 2,4,7-trinitro-9-fluorenone and 2,4-dinitro-9-fluorenone.

Specific examples of the organic pigment serving as a charge generating material in the electrophotographic photoconductor for use in the present invention are azo pigments such as C.I. Pigment Blue 25 (C.I. 21180), C.I. Pigment Red 41 (C.I. 21200) and C.I. Pigment Red 3 (C.I. 5210); phthalocyanine pigments such as C.I. Pigment Blue 16 (C.I. 74100); indigo pigments such as C.I. Pigment Vat Dye (C.I. 73030); and perylene pigments such as Algol Scarlet B and Indanthrene Scarlet R (made by Bayer Co., Ltd.). In addition to the above, inorganic pigments such as selenium, selenium-tellurium, cadmium sulfide and α-silicone can be employed.

Other features of this invention will become apparent in the course of the following description of exemplary embodiments, which are given for illustration of the invention and are not intended to be limiting thereof.

EXAMPLE 1

A mixture of 1.0 g of 5-[4-(di-p-tolylamino)-benzylidene]-5H-dibenzo[a,d]-cycloheptene and 0.2 g of 5%-palladium carbon was added to 50 ml of dioxane. This reaction mixture wa subjected to hydrogenation reaction with hydrogen gas of 1 atom supplied thereto in a shakingtype hydrogenating apparatus over a period of 24 hours. The resulting product was filtered through Celite and the filtrate was evaporated to dryness, so that a colorless oily material was obtained. The colorless oily material was subjected to column chromatography using silica gel as a carrier and a mixed solvent of toluene and n-hexane with a mixing ratio of 2:1 as a developing solvent. The thus obtained reaction product was recrystallized from a mixed solvent of c-hexane and ethanol, whereby 0.7 g of 5-[(4-N,N-di-p-tolylamino)benzyl]-5H-dibenzo[a, d]-cycloheptane having the following formula was obtained in the form of colorless plates.

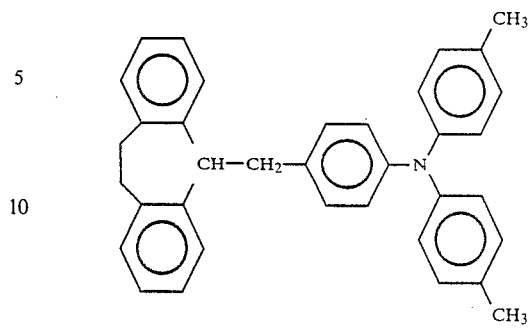

The melting point of the above 5-[(4-N,N-di-p-tolylamino)benzyl]-5H-dibenzo[a,d]-cycloheptane was 148.0 to 149.° C.

The results of the elemental analysis of the thus obtained product were as follows:

|  | % C | % H | % N |
| --- | --- | --- | --- |
| Calculated | 90.13 | 6.95 | 2.92 |
| Found | 89.83 | 6.75 | 2.68 |

The single figure shows an infrared absorption spectrum of the above obtained 5-[(4-N,N-di-p-tolylamino)-benzyl]-5H-dibenzo[a,d]-cycloheptane, taken by use of a KBr tablet.

The results of other analyses are as follows:

MS (70eV) m/e:

28, 286, 479

$^1H_{nmr}$(CDCl$_3$):

δ6.75 to 7.20 (20H,m, Aromatic);

δ4.15 (1H,t, >CH—);

δ2.80 to 3.60 (6H, m, >CH$_2$×3)

δ2.25 (6H, S, —CH$_3$×2);

$^{13}C_{nmr}$(CDCl$_3$):

δ20.72;—CH$_3$×2;

δ33.78;>CH$_2$×2;

δ44.64;>CH$_2$;

δ57.05;>CH—;

δ123.70, 123.97, 125.89, 126.55, 129.78, 129.94, 130.32, 130.79, 131.86, 134.64, 139.84, 141.07, 145.81, 146.31, Aromatic C By use of a similar synthesizing process to the above-mentioned process, 5-[(4-N,N-ditolylamino)benzyl]-5H-dibenzo[a,d]-cycloheptane derivatives, in which the tolylamino moiety is o-tolylamino or m-tolylamino, can be prepared.

APPLICATION EXAMPLE 1

7.5 parts by weight of a bisazo compound having the following formula serving as a charge generating material and 500 parts by weight of a 0.5% tetrahydrofuran solution of polyester resin, "Vylon 200" (Trademark), made by Toyobo Company, were dispersed and ground in a ball mill.

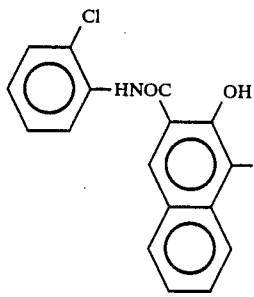 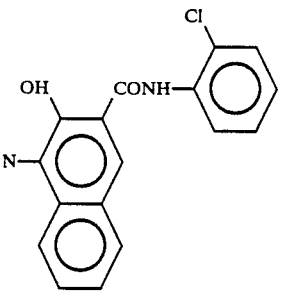

The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

One part by weight of 5-[[4-N,N-di-p-tolylamino)benzyl]-5H-dibenzo[a,d]-cycloheptane prepared in the abovementioned Example 1, serving as a charge transporting material, was dissolved in a resin solution prepared by mixing 1 part by weight of polycarbonate resin, "Panlite K-1300" (Trademark), made by Teijin Limited., and 8 parts by weight of tetrahydrofuran to prepare a solution of the charge transporting material. This solution was coated on the above formed charge generation layer by a doctor blade and then dried at 80° C. for 2 minutes and at 120° C. for 5 minutes, so that a charge transport layer having a thickness of about 20 μm was formed on the charge generation layer. Thus, a two-layered type electrophotographic photoconductor was obtained.

The thus obtained two-layered type electrophotographic photoconductor was charged negatively in the dark under application of −6 kV of corona charge for 20 seconds, using a commercially available electrostatic copying sheet testing apparatus "Paper Analyzer Model SP-428" (Trademark), made by Kawaguchi Electro Works Co., Ltd., and the surface potential $V_m$ (V) of the photoconductor was measured. The electrophotographic photoconductor was then allowed to stand in the dark for 20 seconds without applying any charge thereto, and the surface potential $V_o$ (V) of the photoconductor was measured. The photoconductor was then illuminated by a tungsten lamp in such a manner that the illuminance on the illuminated surface of the photoconductor was 4.5 lux, and the exposure $E_{\frac{1}{2}}$ (lux·sec) required to reduce the initial potential $V_o$ (V) was measured. The results are as follows:

$V_m = -1470$ V
$V_o = -1320$ V
$E_{\frac{1}{2}} = 0.92$ lux·sec

As can be seen from the above results, the electrophotographic photoconductor comprising 5-[(4-N,N-di-p-tolylamino)benzyl]-5H-dibenzo[a,d]-cycloheptane according to the present invention, which serves as a photoconductive material, shows high photosensitivity in the visible light range.

What is claimed is:

1. 5-[(4-N, N-ditolylamino)benzyl]-5H-dibenzo[a,d]-cycloheptane derivatives having formula (I):

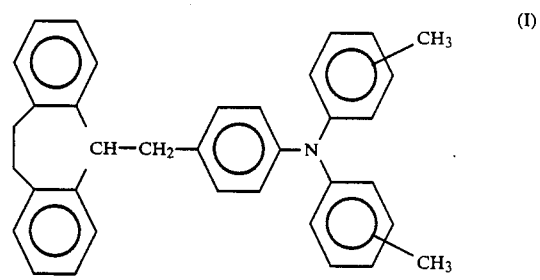

2. 50[(4-N, N-di-p-tolylamino)benzyl]-5H-dibenzo[a,d]-cycloheptane having formula (I-1):

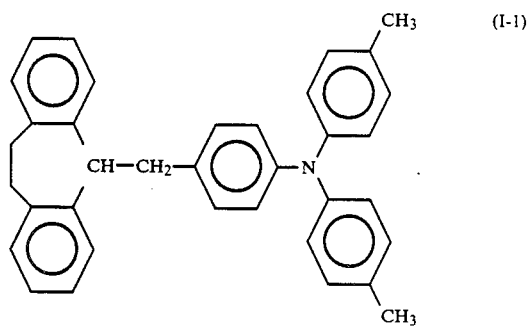

* * * * *